(12) United States Patent
Kim et al.

(10) Patent No.: US 9,907,537 B2
(45) Date of Patent: Mar. 6, 2018

(54) PULLBACK SYSTEM

(71) Applicant: Dongguk University Industry-Academic Cooperation Foundation, Seoul (KR)

(72) Inventors: Sung Min Kim, Goyang (KR); Hong Seok Lim, Seoul (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 168 days.

(21) Appl. No.: 14/553,546

(22) Filed: Nov. 25, 2014

(65) Prior Publication Data

US 2015/0359509 A1 Dec. 17, 2015

(30) Foreign Application Priority Data

Jun. 16, 2014 (KR) ........................ 10-2014-0073103

(51) Int. Cl.
*A61B 8/00* (2006.01)
*A61B 8/12* (2006.01)
*G01S 7/52* (2006.01)

(52) U.S. Cl.
CPC .............. *A61B 8/4461* (2013.01); *A61B 8/12* (2013.01); *A61B 8/445* (2013.01); *A61B 2562/222* (2013.01); *G01S 7/52079* (2013.01)

(58) Field of Classification Search
CPC ......... A61B 8/12; A61B 8/4461; A61B 8/445; A61B 2562/222
See application file for complete search history.

(56) References Cited

U.S. PATENT DOCUMENTS

| 5,383,460 A * | 1/1995 | Jang .................... A61B 8/12 600/439 |
| 6,013,030 A * | 1/2000 | Webler .................... A61B 8/12 128/916 |

(Continued)

FOREIGN PATENT DOCUMENTS

| JP | H07-163562 A | 6/1995 |
| JP | 2003-93386 A | 4/2003 |

(Continued)

OTHER PUBLICATIONS

Hong Seok Lim et al., "Study on the behavior characteristics of longitudinal length variation mechanism for rotating axis", Symposium of The Korean Society of Mechanical Engineers, Dec. 18, 2013, pp. 3098-3100.

*Primary Examiner* — Long V Le
*Assistant Examiner* — Angela M Hoffa

(57) ABSTRACT

Disclosed is a pullback system, which has a simplified and miniaturized structure and an advanced function. The pullback system includes a central unit, which includes a rotation transducer part that rotates, and a stretchable part that is connected to a side of the rotation transducer part to rotate together with the rotation transducer part and that has a stretchable property, and a first unit rotatably coupled to a portion of the central unit. As the first unit moves in a first direction oriented from the rotation transducer part to the stretchable part or in a second direction opposite to the first direction, the stretchable part contacts or stretches.

7 Claims, 6 Drawing Sheets

(56) References Cited

U.S. PATENT DOCUMENTS

| | | | | |
|---|---|---|---|---|
| 6,292,681 B1* | 9/2001 | Moore | A61B 8/12 | 600/407 |
| 6,413,222 B1* | 7/2002 | Pantages | A61B 8/12 | 600/466 |
| 6,517,528 B1* | 2/2003 | Pantages | A61B 8/12 | 600/459 |
| 6,641,546 B2* | 11/2003 | White | A61B 8/12 | 600/466 |
| 6,758,818 B2* | 7/2004 | Pantages | A61B 8/12 | 600/466 |
| 6,827,693 B2* | 12/2004 | White | A61B 8/12 | 600/466 |
| 7,077,808 B2* | 7/2006 | Couvillon, Jr. | A61B 8/12 | 600/466 |
| 7,658,715 B2* | 2/2010 | Park | A61M 25/0158 | 600/437 |
| 7,916,170 B2* | 3/2011 | Soltysik | H04N 5/84 | 348/92 |
| 8,187,193 B2* | 5/2012 | Park | G01S 7/52079 | 600/459 |
| 8,632,467 B2* | 1/2014 | Levy | A61B 8/12 | 600/139 |
| 8,652,050 B2* | 2/2014 | Park | G01S 7/52079 | 600/459 |
| 9,307,911 B2* | 4/2016 | Levy | A61B 8/12 | |
| 2002/0151799 A1* | 10/2002 | Pantages | A61B 8/12 | 600/466 |
| 2009/0216125 A1* | 8/2009 | Lenker | A61B 8/12 | 600/445 |
| 2009/0240242 A1 | 9/2009 | Neuberger | | |
| 2011/0106019 A1* | 5/2011 | Bagwell | A61B 1/018 | 604/267 |
| 2011/0263986 A1* | 10/2011 | Park | A61B 8/4461 | 600/462 |
| 2012/0130243 A1 | 5/2012 | Balocco et al. | | |
| 2015/0359509 A1* | 12/2015 | Kim | A61B 8/12 | 600/467 |

FOREIGN PATENT DOCUMENTS

| | | |
|---|---|---|
| JP | 2013-543786 A | 12/2013 |
| KR | 10-2009-0082901 A | 7/2009 |
| KR | 10-2010-0138977 A | 12/2010 |

* cited by examiner

PULLBACK SYSTEM

CROSS-REFERENCE TO RELATED APPLICATION

The priority of Korean patent application No. 10-2014-0073103 filed on Jun. 16, 2014, the disclosure of which is hereby incorporated in its entirety by reference, is claimed.

BACKGROUND

1. Field of the Invention

The present invention relates to a pullback system, which has a simplified and miniaturized structure and an advanced function.

2. Background of the Invention

As ultrasonic technologies are gradually developed, ultrasonic mechanisms can be miniaturized to be inserted into a blood vessel of a human body and be used to analyze a state of a blood vessel such as an artery. This technique is called intravascular ultrasound (IVUS). To this end, using the speed of a sound, a time taken to transmit a vibration and to receive an ultrasound can be converted to a measurement of a distance or a depth.

Intravascular ultrasound is used for peripheral blood vessel as well as coronary arteries, and is referred to as intracoronary ultrasound, specifically, for the heart. Ultrasound having a diameter of about 1 mm may be used to observe the inside of a blood vessel. The state and type of an intracoronary lesion, and the degree and length of angiostenosis can be accurately analyzed using intravascular ultrasound. In plain language, intravascular ultrasound technologies are used to observe the inside of blood vessels.

Unlike two-dimensional shadow images according to coronary angiography, intravascular ultrasound uses a ultrasound that is directly introduced into a blood vessel, so that an observer can see the inside of the blood vessel, and thus, can understand and treat the blood vessel more accurately.

An ultrasonic catheter including a rotation transducer may be inserted into a blood vessel to perform an intravascular ultrasound process, thereby accurately analyzing an inner state of the blood vessel, such as a degree of hardening of a wall of the blood vessel and a degree of calcification thereof. Such a rotation transducer is inserted into an artery and is moved to a target region. In addition, the rotation transducer generates and receives ultrasonic pulses for forming and displaying an image of the surface shape and inner structure of the target region.

A 360-degree view of the inside of a blood vessel should be provided to perfectly depict target regions. To this end, the rotation transducer is rotated through 360 degrees. This is the reason why the term "rotation" is included in the name thereof.

In addition, the rotation transducer should be uniformly moved in the longitudinal direction thereof to scan long cell regions such as a blood vessel. To this end, a pullback system is needed as a pulling device.

To sum up, a pullback system for a catheter including a rotation transducer (hereinafter, referred to as just a pullback system) rotates the rotation transducer, and simultaneously, performs a pullback operation.

Referring to patent document 1, a conventional pullback system used for IVUS rotates a catheter including a rotation transducer by using a motor as a driving source, and simultaneously, performs a pullback operation for pulling the whole of the conventional pullback system at a constant speed. However, the conventional pullback system has the following limitations.

First, since the conventional pullback system uses a method of pulling the whole of a system for rotating the catheter including the rotation transducer, the entire structure of the conventional pullback system is enlarged and complicated, which may increase production costs and the weight and size of a device.

Secondly, when a structure that pulls back the whole of a device for rotating the catheter including the rotation transducer is provided, the catheter may be pulled back in a bending state. In this case, an error occurrence probability of a pulling distance is increased. An error in measuring a distance may decrease the accuracy of an intravascular diagnosis.

CITED DOCUMENT

[Patent Document 1] Korean Patent Publication No. 10-2009-0082901

SUMMARY

Various embodiments of the invention are directed to providing a pullback system, the entire structure of which is simplified and miniaturized and which decreases the size and weight of a device and prevents the occurrence of an error in measuring a pullback distance.

According to an embodiment of the present invention, a pullback system includes: a central unit, which includes a rotation transducer part that rotates, and a stretchable part that is connected to a side of the rotation transducer part to rotate together with the rotation transducer part and that has a stretchable property; and a first unit rotatably coupled to a portion of the central unit, wherein as the first unit moves in a first direction oriented from the rotation transducer part to the stretchable part or in a second direction opposite to the first direction, the stretchable part contacts or stretches.

DETAILED DESCRIPTION

Hereinafter, preferred embodiments of the present invention will be described in detail with reference to the accompanying drawings. However, the present invention is not limited to the following embodiments.

An Embodiment

Figure 1:
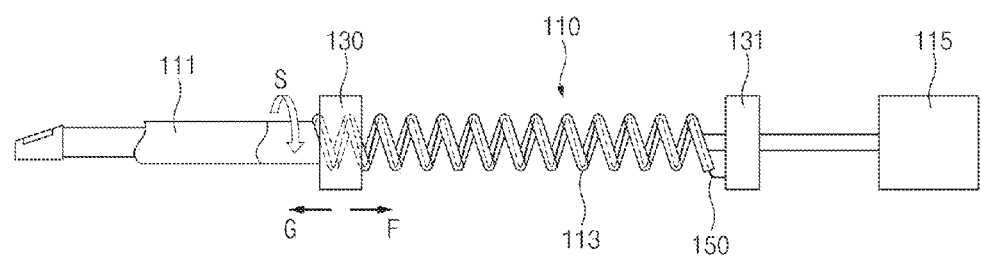
FIG. 1 is a side view illustrating a pullback system according to an embodiment of the present invention.
Figure 2:
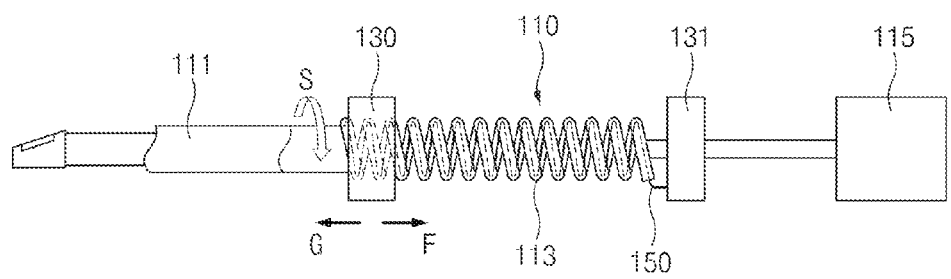
FIG. 2 is a side view illustrating a pullback state of a rotation transducer in the pullback system of FIG. 1.
Figure 3:
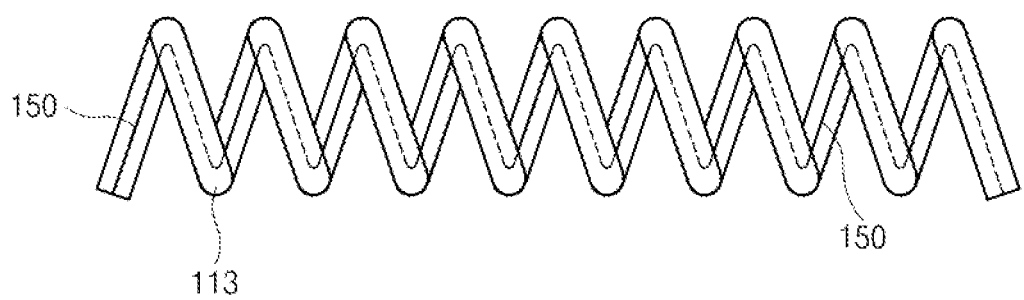
FIG. 3 is an enlarged view illustrating a stretchable part in the pullback system of FIG. 1.
Figure 4:
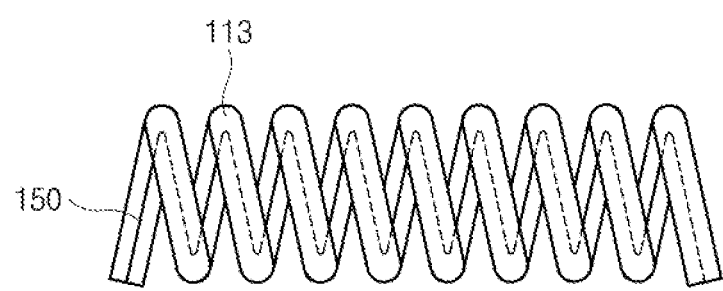
FIG. 4 is an enlarged view illustrating the stretchable part in the pullback system of FIG. 2.

FIG. 1 is a side view illustrating a pullback system according to an embodiment of the present invention. FIG. 2 is a side view illustrating a pullback state of a rotation transducer in the pullback system of FIG. 1. FIG. 3 is an enlarged view illustrating a stretchable part in the pullback system of FIG. 1. FIG. 4 is an enlarged view illustrating the stretchable part in the pullback system of FIG. 2.

Hereinafter, a pullback system according to an embodiment of the present invention will now be described with reference to FIGS. 1 to 4.

Referring to FIGS. 1 and 2, the pullback system according to the current embodiment includes a central unit 110 and a first unit 130.

The central unit 110 includes: a rotation transducer part 111, which undergoes a rotation S and transmits and receives an ultrasonic signal; and a stretchable part 113 which is connected to a side of the rotation transducer part 111 and rotates together with the rotation transducer part 111. An end of the stretchable part 113 may be connected to the rotation transducer part 111, and the other end thereof may be connected to a rotary motor 115. In this case, torque may be transmitted from the rotary motor 115 to the stretchable part 113 to rotate the stretchable part 113, and the stretchable part 113 and the rotation transducer part 111 connected to the stretchable part 113 may undergo the rotation S, together.

The rotation transducer part 111 not only transmits and receives an ultrasonic signal, but also converts the ultrasonic signal and an electrical signal into each other. Thus, the rotation transducer part 111 may be referred to as just a transducer. The rotation transducer part 111 rotates through 360 degrees according to a rotation of the rotary motor 115. Accordingly, the whole of a circumference of a blood wall is diagnosed.

The stretchable part 113 may be formed of a stretchable material. Thus, the stretchable part 113 is stretched by tensile force and is compressed by compressive force. The stretchable part 113 may have a spring shape that extends into a spiral shape.

The first unit 130 is rotatably coupled to a portion of the central unit 110. The first unit 130 may be coupled to an end part of the stretchable part 113 in a second direction G.

In this case, the first unit 130 may be bearing-coupled to the stretchable part 113. This means that the first unit 130 is coupled to the stretchable part 113 through a bearing. In this case, even when the first unit 130 is not rotated, the central unit 110 including the stretchable part 113 is allowed to be rotated. Since bearing coupling between a shaft and a unit surrounding the shaft is well known in the art, a detailed description thereof will be omitted here.

The first unit 130 coupled to the stretchable part 113 through the bearing is allowed to move in both a first direction F and the second direction G. The first direction F is oriented from the rotation transducer part 111 to the stretchable part 113, and the second direction G is opposite to the first direction F.

When the first unit 130 moves in the first direction F, the stretchable part 113 may contract corresponding to it. In other words, when the first unit 130 coupled to the end part of the stretchable part 113 moves in the first direction F, compressive force is applied to the stretchable part 113 to decrease the length of the stretchable part 113. Since the first unit 130 is coupled to the stretchable part 113 through the bearing, while the length of the stretchable part 113 is decreased, a rotation thereof is maintained.

When the stretchable part 113 contracts, the rotation transducer part 111 connected to the end of the stretchable part 113 moves in the first direction F. In this manner, the rotation transducer part 111 is pulled back in the first direction F (refer to FIG. 2).

When the first unit 130 moves in the second direction G opposite to the first direction F, the stretchable part 113 may stretch corresponding to it. In other words, when the first unit 130 coupled to the stretchable part 113 moves in the second direction G, tensile force is applied to the stretchable part 113 to increase the length of the stretchable part 113. Since the first unit 130 is coupled to the stretchable part 113 through the bearing, while the length of the stretchable part 113 is increased, a rotation thereof is maintained.

When the stretchable part 113 stretches, the rotation transducer part 111 connected to the end of the stretchable part 113 moves in the second direction G. In this manner, the rotation transducer part 111 is returned to an original position thereof (refer to FIG. 1).

The pullback system may further include a second unit 131 spaced a predetermined distance from the first unit 130 in the first direction F.

Like the first unit 130, the second unit 131 may be bearing-coupled to the central unit 110. Thus, even when the central unit 110 rotates, the second unit 131 may be prevented from rotating. The second unit 131 may be coupled to a portion of the central unit 110 except for the stretchable part 113. Specifically, the second unit 131 may be fixed without moving in the first direction F or the second direction G.

The second unit 131 may function as a reference position for the first unit 130. For example, when the first unit 130 is moved in the first direction F, a structure for pulling the first unit 130 may be installed using the second unit 131 as a support point. In this case, the second unit 131 may be fixed, and the first unit 130 may be moved in the first direction F or the second direction G.

The second unit 131 may not only function as a reference support point, but also improve rotation stability. If the first unit 130 is provided without the second unit 131, when the central unit 110 rotates, only the first unit 130 guides or supports the rotation of the central unit 110. However, when the first unit 130 and the second unit 131 are provided, the first unit 130 and the second unit 131 guide or support the rotation of the central unit 110 at two points, so that a rotation shaft of the central unit 110 can rotate more stably.

Referring to FIGS. 3 and 4, the pullback system may further include a signal cable 150 through which a signal transmitted to or received from the rotation transducer part 111 moves. In this case, the signal cable 150 may be attached to the stretchable part 113 along the spiral shape thereof.

Referring to FIG. 3, the stretchable part 113 to which the signal cable 150 is attached stretches. Referring to FIG. 4, the stretchable part 113 to which the signal cable 150 is attached contracts.

Since the signal cable 150 is attached to the stretchable part 113 along the spiral shape thereof, when the rotation transducer part 111 is pulled in the first direction F, the signal cable 150 is prevented from being bent or folded. If the signal cable 150 is bent or folded, an electric current may be concentrated in a bent or folded portion of the signal cable 150 to heat the bent or folded portion. Such heating can be prevented by attaching the signal cable 150 to the stretchable part 113 along the spiral shape thereof.

In addition, since the signal cable 150 is prevented from being bent or folded, a breakage of the signal cable 150 caused by repeated bending, or short circuiting caused by the breakage is also prevented.

The pullback system uses a method of pulling the rotating shaft, that is, the central unit 110, instead of using a method of pulling the whole of a system for rotating a rotation transducer part, thereby preventing the entire structure of the pullback system from being enlarged and complicated, and simplifying and miniaturizing the entire structure of a system. Accordingly, the weight and size of a device can be significantly decreased.

In addition, the pullback system uses the method of pulling the rotatable rotation shaft, thereby preventing a catheter from being pulled back in a bending state, and reducing an error occurrence probability of a pulling distance. Accordingly, the accuracy of an intravascular diagnosis can be improved.

Another Embodiment

Figure 5:
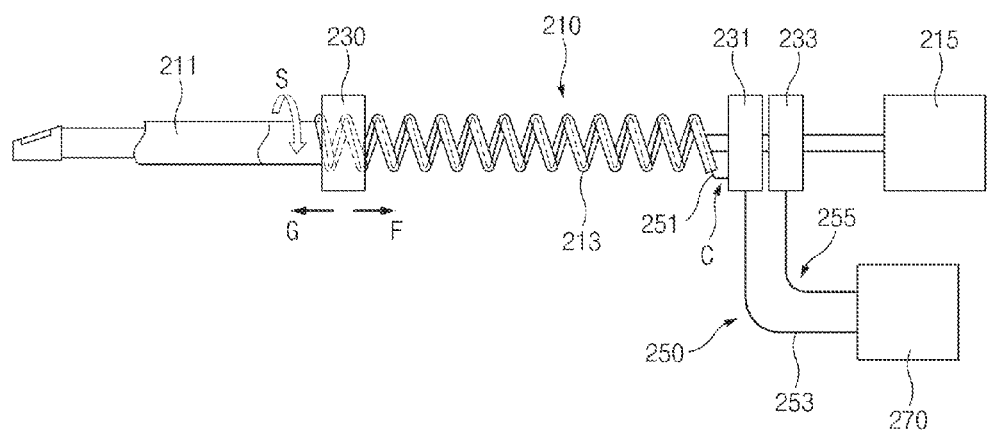
FIG. 5 is a side view illustrating a pullback system according to another embodiment of the present invention.

FIG. 5 is a side view illustrating a pullback system according to an embodiment of the present invention.

The pullback system according to the current embodiment has a configuration similar to that of the pullback system according to the previous embodiment. However, the pullback system according to the current embodiment is different from the pullback system according to the previous embodiment in that the former further includes a signal transceiver module.

Parts, which are the same as (or correspond to) the previously-described parts, are denoted by the same (or corresponding) reference numerals, and a detailed description thereof will be omitted. Hereinafter, the pullback system according to the current embodiment will now be described with reference to FIG. 5.

The pullback system according to the current embodiment may further include a signal transceiver module 270 which transmits a signal, such as an electrical or ultrasonic signal, to a rotation transducer part 211 or receives the signal therefrom. In this case, the rotation transducer part 211 and the signal transceiver module 270 may be connected to each other through signal cables 250 and 255 for moving an electrical or ultrasonic signal.

The electrical signal may be used to supply electrical energy to the rotation transducer part 211, and the ultrasonic signal may be a signal having an ultrasound form obtained from an intravascular state by a rotation transducer.

A signal cable may be provided as a single line. In this case, the signal cable may be referred to as a first signal cable 250 for convenience in description. The first signal cable 250 may include a first cable part 251 and a second cable part 253.

The first cable part 251 extends from the rotation transducer part 211 and maintains a contact state with a second unit 231. While the first cable part 251 extends from the rotation transducer part 211, the first cable part 251 may be attached to a central unit 210. Accordingly, a first cable is allowed to rotate together with the central unit 210. In this case, a part C of the first cable part 251 maintains a contact state with the second unit 231, and simultaneously, is allowed to rotate together with the central unit 210.

The second cable part 253 connects the signal transceiver module 270 to the second unit 231. In this case, an end part of the second cable part 253 is connected to the second unit 231.

In this case, the second unit 231 is not rotated.

The second unit 231 is formed of a material through which an electrical or ultrasonic signal passes. Thus, the first cable part 251 and the second cable part 253 are electrically connected to each other through the second unit 231 and transmit a signal to each other.

The above-described configuration of the pullback system according to the current embodiment prevents the first signal cable 250, which connects the rotation transducer part 211 and the signal transceiver module 270 to each other, from being twisted by a rotation of the central unit 210 including the rotation transducer part 211.

When the signal cable is constituted by two cable lines, one of the cable lines may be referred to as the first signal cable 250, and the other may be referred to as a second signal cable 255.

Twisting of the second signal cable 255 is prevented in the same manner as that of the first signal cable 250. That is, a third unit 233 having the same configuration as that of the second unit 231 may be installed on a side part of the second unit 231 and be rotatable about the central unit 210, and the second signal cable 255 may be connected to the rotation transducer part 211 through the third unit 233 like the second unit 231.

Thus, although the signal cable is constituted by two cable lines, the central unit 210 is allowed to rotate without twisting the signal cable.

The connecting of the second signal cable 255 to the rotation transducer part 211 through the third unit 233 is the same as the connecting of the first signal cable 250 to the rotation transducer part 211 through the second unit 231, and thus, a description thereof will be omitted.

Another Embodiment

Figure 6:
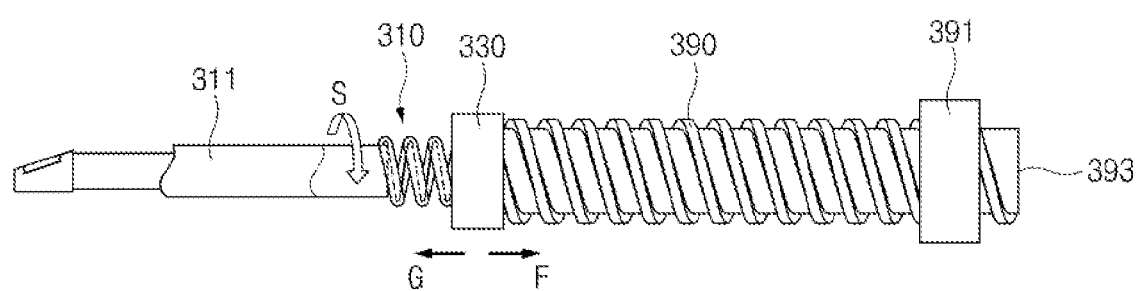
FIG. 6 is a side view illustrating a pullback system according to another embodiment of the present invention.

FIG. 6 is a side view illustrating a pullback system according to an embodiment of the present invention.

The pullback system according to the current embodiment has a configuration similar to that of the pullback system according to the embodiment of FIG. 1. However, the pullback system according to the current embodiment is different from the pullback system according to the embodiment of FIG. 1 in that the former further includes a screw unit.

Parts, which are the same as (or correspond to) the previously-described parts, are denoted by the same (or corresponding) reference numerals, and a detailed description thereof will be omitted. Hereinafter, the pullback system according to the current embodiment will now be described with reference to FIG. 6.

The pullback system according to the current embodiment may further include a screw unit 390 and a nut unit 391. The screw unit 390 may be coupled to a first unit 330, and the nut unit 391 may be coupled to the screw unit 390.

An end of the screw unit 390 may be attached to the first unit 330, and an outer circumferential surface thereof may be provided with a screw thread. The nut unit 391 may be coupled to the other end of the screw unit 390. An inner circumferential surface of the nut unit 391 may be provided with a screw thread corresponding to the screw thread formed on the outer circumferential surface of the screw unit 390.

The nut unit 391 may be fixed without moving in a first direction F or a second direction G. In this case, when the nut unit 391 rotates, the screw unit 390 moves in the first direction F or the second direction G. At this point, the first unit 330 is also moved in the first direction F or the second direction G according to the movement of the screw unit 390 since the first unit 330 is attached to the screw unit 390. When the first unit 330 moves in the first direction F, a rotation transducer part 311 may be pulled in the first direction F. When the first unit 330 moves in the second direction G, the rotation transducer part 311 may be returned to an original position thereof. In this case, the rotation transducer part 311 may rotate in a direction S, and simultaneously, move in the first direction F or the second direction G.

The screw unit 390 may include a hole 393 passing therethrough. A central unit 310 may be disposed in the hole 393. The central unit 310 is rotatably coupled to the first unit 330 through a bearing and rotates in the hole 393. Thus, the first unit 330 and the screw unit 390 attached to the first unit 330 may not affect the rotation of the central unit 310. In a same manner, the central unit 310 may not affect the rotation of the screw unit 390.

When the screw unit 390 has a precise screw pitch, the rotation transducer part 311 may be accurately moved by about 0.1 mm or smaller. In this case, a displacement of the central unit 310 in a longitudinal direction thereof (the first direction F or the second direction G) is accurately adjusted to correspond to a desired amount just by using a hall sensor that measures a rotation angle and that may be included in a motor (not shown) for rotating the nut unit 391.

A pullback system according to the present invention includes: a central unit including a rotation transducer and a stretchable part; and a first unit rotatably coupled to a portion of the central unit, thereby simplifying and miniaturizing the entire structure of the pullback system, decreasing the size and weight of a device, and preventing the occurrence of an error in measuring a pullback distance.

While all the embodiments and specified examples of the present disclosure have been particularly described to help those skilled in the art to understand the principles and concepts of the present invention, it will be understood by those skilled in the art that changes may be made therein without departing from the spirit and scope of the present invention. Thus, the disclosed embodiments should be considered in descriptive sense only and not for purposes of limitation. The scope of the present invention is defined not by the foregoing detailed description but by the appended claims, and all differences within the scope will be construed as being included in the present invention.

What is claimed is:

1. A pullback system comprising:
    a central unit, which includes an ultrasonic transducer that rotates around an axis parallel to a longitudinal direction, and a stretchable part that is connected to a side of the ultrasonic transducer to rotate together with the ultrasonic transducer, the stretchable part having a stretchable property;
    a first unit coupled to the stretchable part and configured to move in a first direction oriented from the ultrasonic transducer to the stretchable part along the axis to apply a compressive force to the stretchable part and in a second direction opposite to the first direction to apply a tensile force to the stretchable part;
    a second unit spaced a predetermined distance from the first unit in the first direction, wherein the second unit is rotatably coupled to the stretchable part;
    a screw unit coupled to the first unit; and
    a nut unit screwed to the screw unit,
    wherein when the first unit moves in the first direction relative to the second unit, the stretchable part contracts, and the ultrasonic transducer connected to the stretchable part moves in the first direction while rotating,
    wherein when the first unit moves in the second direction relative to the second unit, the stretchable part stretches and the ultrasonic transducer connected to the stretchable part moves in the second direction while rotating,
    wherein the ultrasonic transducer transmits and receives an ultrasonic signal and converts the ultrasonic signal and an electrical signal into each other, and
    wherein the first unit is moved in the first or second direction according to a rotation of the nut unit relative to the screw unit.

2. The pullback system according to claim 1, wherein the stretchable part has a spring shape that extends into a spiral shape.

3. The pullback system according to claim 2, further comprising a signal cable through which a signal transmitted to or received from the ultrasonic transducer moves,
    wherein the signal cable is attached to the stretchable part along the spiral shape thereof.

4. The pullback system according to claim 1, wherein the first unit is coupled to the stretchable part through a bearing.

5. The pullback system according to claim 1, wherein the second unit is coupled to the stretchable part through a bearing.

6. The pullback system according to claim 1, further comprising a signal transceiver module which transmits a signal to the ultrasonic transducer or receives the signal therefrom,
    wherein the ultrasonic transducer and the signal transceiver module are connected to each other through a signal cable for moving the signal,
    the signal cable includes a first cable part that maintains a contact state with the second unit and that rotates together with the central unit, and a second cable part that is connected to the second unit and that does not rotate, and
    the first cable part and the second cable part transmit the signal to each other through the second unit.

7. The pullback system according to claim 1, wherein the screw unit has a hole therein, and the stretchable part is disposed in the hole.

* * * * *